(12) United States Patent
Wright et al.

(10) Patent No.: US 8,584,539 B2
(45) Date of Patent: Nov. 19, 2013

(54) DELIVERY DEVICE FOR DISPENSING PHARMACEUTICAL DOSAGE FORMS INTO DISSOLUTION TESTING APPARATUS

(75) Inventors: Daryl E Wright, Fairless Hill, PA (US); Lyn Hughes, Harleysville, PA (US); Donald F Wright, Richboro, PA (US)

(73) Assignee: Rohm and Haas Company, Philadelphia, PA (US)

( * ) Notice: Subject to any disclaimer, the term of this patent is extended or adjusted under 35 U.S.C. 154(b) by 397 days.

(21) Appl. No.: 13/167,812

(22) Filed: Jun. 24, 2011

(65) Prior Publication Data

US 2012/0000275 A1    Jan. 5, 2012

Related U.S. Application Data

(60) Provisional application No. 61/398,750, filed on Jun. 30, 2010.

(51) Int. Cl.
*G01N 33/15* (2006.01)

(52) U.S. Cl.
USPC .......................................................... 73/866

(58) Field of Classification Search
USPC .......................................................... 73/866
See application file for complete search history.

(56) References Cited

U.S. PATENT DOCUMENTS

| | | | |
|---|---|---|---|
| 3,791,222 A * | 2/1974 | Goodhart et al. | 73/866 |
| 3,801,280 A | 4/1974 | Shah et al. | |
| 3,802,272 A * | 4/1974 | Bischoff et al. | 73/866 |
| 4,335,438 A * | 6/1982 | Smolen | 702/19 |
| 4,506,985 A * | 3/1985 | Buchfink | 366/107 |
| 4,681,858 A * | 7/1987 | Chaudhari et al. | 436/165 |
| 4,855,821 A * | 8/1989 | Swon et al. | 348/89 |
| 4,856,909 A * | 8/1989 | Mehta et al. | 366/208 |
| 5,412,979 A * | 5/1995 | Fassihi | 73/53.01 |
| 5,589,649 A * | 12/1996 | Brinker et al. | 73/866 |
| 5,807,115 A | 9/1998 | Hu | |
| 5,816,701 A * | 10/1998 | Martin et al. | 366/208 |
| 5,827,984 A * | 10/1998 | Sinnreich et al. | 73/866 |
| 6,060,024 A | 5/2000 | Hutchins et al. | |
| 6,308,584 B1 | 10/2001 | Benz | |
| 6,799,123 B2 | 9/2004 | Hughes | |
| 7,021,163 B2 * | 4/2006 | Kyne | 73/866 |
| 2007/0092404 A1 | 4/2007 | Hughes et al. | |
| 2007/0160497 A1 | 7/2007 | Hughes et al. | |

FOREIGN PATENT DOCUMENTS

EP    2199773 A1    6/2010

* cited by examiner

*Primary Examiner* — John Fitzgerald
(74) *Attorney, Agent, or Firm* — Carl P. Hemenway

(57) ABSTRACT

The present invention provides a dissolution test cell having a chamber and slide valve for dispensing pharmaceutical dosage forms, such as tablets, capsules, and powders, into the chamber without having to open the cell and expose the chamber and its contents to the ambient environment. The present invention also facilitates removal of a partially dissolved or non-disintegrating dosage form from the chamber and cell entirely, without exposing the interior of the cell and chamber. Dissolution test apparatus comprising at least one dissolution test cell in accordance with the invention is also provided, as well as methods for its operation to obtain Level A IVIVC dissolution results which accurately correlate with in vivo dissolution results are also provided.

6 Claims, 9 Drawing Sheets

DELIVERY DEVICE FOR DISPENSING PHARMACEUTICAL DOSAGE FORMS INTO DISSOLUTION TESTING APPARATUS

This patent application claims the benefit of priority under 35 U.S.C. §119(e) of U.S. Provisional Patent Application No. 61/398,750 filed on Jun. 30, 2010.

FIELD OF THE INVENTION

The present invention relates to an apparatus and method of use of same for dissolution testing of pharmaceutical dosage forms. In particular, the present invention relates to a continuous flow cell having a chamber and a valve assembly for allowing dispensation and removal of pharmaceutical dosage forms, such as tablets, capsules, and powders, into and out of the chamber without having to open the cell and expose its content to the ambient environment. Furthermore, the apparatus of the present invention facilitates removal of a partially dissolved or non-disintegrating dosage form from the chamber and cell entirely, without exposing the interior of the cell and chamber.

BACKGROUND OF THE INVENTION

The rate at which pharmaceutically active compounds dissolve in gastrointestinal fluids is of crucial importance in the design and use of orally administered medications. The active compound must be dissolved before it can be absorbed by the body. The rate at which the active substance enters into solution is known in the art as the dissolution rate, and the determination of the dissolution rate in vitro is known as dissolution testing.

Dissolution testing provides a better understanding of the amount of a pharmaceutically active compound that is available at a particular absorption site at various times. In addition, establishing a relationship between dosage form and availability of one or more pharmaceutically active compounds at certain absorption sites, as well as the systemic blood levels of such active compounds, facilitates the development of specialized delivery techniques.

The concept of using in vitro data to predict or model in vivo behavior, referred to as in vitro-in vivo correlation, or IVIVC, is of great interest to practitioners in the pharmaceutical and medical industries, among others. Test methods with good IVIVC are much more capable of detecting problems with existing formulations and in the development of new formulations. Systems which correlate closely with the dissolution and absorption data obtained in vivo can be used in developing dosage forms as well as in the production, scale-up, determination of lot-to-lot variability, testing of new dosage strengths, testing of minor formulation changes, testing after changes in the site of manufacture and for determining bio-equivalence.

Various methods and devices for dissolution measurement are well known and described in the art.

The US Food and Drug Administration (US FDA) has issued guidelines on the relative value of different levels of correlation that are more or less desirable in in vitro testing (Guidance for Industry, Extended Release Oral Dosage Forms: Application of In vitro/In vivo Correlations, September 1997). A "Level A" correlation is one that predicts the entire in vivo time course from the in vitro data. A "Level B" correlation is one that uses statistical moment analysis. The mean dissolution time is compared either to the mean residence time or to the mean in vivo dissolution time. A "Level C" correlation establishes a single point relationship between a dissolution parameter and a pharmacokinetic parameter.

Level B and Level C correlations do not reflect the complete shape of the plasma concentration-time curve, which is a graphical representation of the changes in concentration of one or more active substances over the time required for the active substances to pass through the patient's body. Thus, A Level A correlation is considered to be the most informative and is recommended by the USFDA wherever possible. Having a high level of correlation, e.g., a Level A correlation, can reduce the amount of in vivo testing necessary for new formulations and can, therefore, be very valuable to practitioners.

In many previously developed flow-through dissolution testing systems, only one cell was used per test. There are multiple cell systems available commercially, but the cells in these systems are arranged in parallel so that each cell is independent of the other and, hence, they function as a plurality of single cell systems. Furthermore, such systems used cells which were in open communication with the environment. In other words, the one or more cells used in earlier dissolution testing systems had no lids or covers and, therefore, fluids could be freely exchanged between the chambers and the ambient environment, whether or not intended by the users.

The United States Pharmcopeia (USP) is a non-governmental, official public standards-setting authority for prescription and over-the-counter medicines and other healthcare products manufactured or sold in the United States. USP also sets widely recognized standards for food ingredients and dietary supplements, including standards for the quality, purity, strength, and consistency of such products. The USP (USP24, pages 1941-1951) describes seven different sets of apparatus for performing dissolution testing. Apparatus 1 and 2 in section <711> (pages 1941-1942) are essentially containers with a suitable stirring device into which is placed a fixed volume of dissolution medium, and the formulation being tested. Samples of the medium are withdrawn at various times and analyzed for dissolved active substance to determine the rate of dissolution. Section <724> (pages 1944-1951) describes various apparatus designed to test dissolution of extended release, delayed release, and transdermal delivery systems. Apparatus 3 (extended release) uses a reciprocating cylinder, Apparatus 4 (extended release) uses a flow-through cell, Apparatus 5 (transdermal) utilizes a paddle over a disk, Apparatus 6 (transdermal) uses a cylinder design, and Apparatus 7 (transdermal) uses a reciprocating holder. Apparatus 1, 2, 3, 5, 6, and 7 use a fixed volume of the dissolution medium. Apparatus 4 uses a continuous flow of dissolution medium. In all cases the volume of dissolution medium used is sufficient to completely dissolve the test substance, frequently known as sink conditions.

For many active substances and dosage forms the principles behind the USP dissolution tests are limiting. These limitations are true for those active substances for which the rate of dissolution is dependent upon the amount of said active substances already dissolved in the release medium. These include, but are not limited to complexes between active substances and ion exchange resins, and poorly soluble active substances. Some combinations of ion exchange resin and active substances form an equilibrium state under fixed volume conditions such that some of the drug remains on the resin, even at infinite time and under sink conditions. This will give rise to incomplete dissolution when using test methods similar to those described in USP24. When an active substance has been dissolved in the gastrointestinal system it is absorbed by the body through the walls of the gastrointestinal system. This results in a decrease in the concentration of the active substance in solution. In the case where the active substance is in equilibrium with the polymeric complex, as described above, this decrease in concentration will displace the equilibrium such that more active substance will be released. As absorption by the body continues, the release of drug from the polymeric complex will be essentially complete. It is therefore clear that the in vitro test as described above, indicating incomplete release, is not predictive of the actual release experienced in vivo. A similar deficiency will occur with poorly soluble materials when sink conditions do not occur in vivo. The concentration will reach saturation, and the dissolution rate will then depend on the rate of absorption of the active substance by the body. The fixed volume limitation does not apply to the flow-through equipment (Apparatus 4 as described in USP 24). In this case the test material is constantly exposed to fresh dissolution medium, where the concentration of active substance is always zero. While this eliminates the equilibrium constraint, and therefore does permit the complete dissolution of such active substances, it still does not accurately simulate the actual physiological condition wherein the concentration of active substance is zero only at the start. With formulations controlled by equilibrium or limited solubility, it is clear to one skilled in the art that the USP methods cannot be expected to give good IVIVC without further mathematical manipulation of the data.

In the current art, Level A IVIVC is generally obtained by the use of mathematical tools to convert the in vitro data into predicted plasma concentration curves, or similar pharmacokinetic data that reflect the entire time course of the drug in the body (i.e., the total time required for the active substance(s) to pass through the body). While this is currently acceptable to the regulatory authorities, it is not completely satisfactory. The value of a mathematical model is frequently related to the number of independent variables used to adjust the model to fit the in vivo data and, as a guideline the USFDA, recommends no more than three independent variables.

The conditions that affect rate of dissolution in the gastrointestinal system are known to vary with position of the active substance(s) in the body's gastro-intestinal system. There have been attempts to simulate these local variations in in vitro testing. One main focus has been on the very large pH change between the stomach and upper GI. This change is large enough to have a very serious effect on the solubility of some active substances. For example, diclofenac sodium is essentially insoluble at the low pH of the stomach, but is soluble at the near neutral conditions of the upper GI. In the current art this change of pH has been addressed in two ways. The first has been to change the fluid used in the dissolution test, for example start with gastric fluid and then empty and refill the test apparatus with intestinal fluid. The second has been to change the pH of the fluid in the test apparatus gradually, while running the test, by addition of a higher pH solution. Neither of these methods adequately simulates the pH change in vivo because in both methods all of the formulation experiences the pH change at the same time, whereas in vivo the pH change is controlled by gastric emptying, which causes a gradual transfer of the disintegrated formulation so that different portions of the formulation experience the pH changes at different times. In U.S. Pat. No. 5,807,115, Hu states that it is difficult to move an already disintegrated solid sample. Hu uses this conclusion to justify the gradual change of pH described above. A method that has been used to solve the problem associated with the USP fixed volume and flow-through methods has been the continuous flow cell, or chamber, in which either the contents of the cell or chamber are stirred, or a part of the effluent is recycled to the cell or chamber. This allows equilibrium effects to be simulated and evaluated.

Previous techniques for correlating in vitro and in vivo dissolution data have, generally, been limited to accounting for such factors as interactions with salts, enzymes, the ionic strength and pH of the medium and temperature. Discrepancies between in vitro and in vivo values of dissolution and absorption have previously been corrected for by transformation of data using functions added to existing mathematical models, such as by applying intestinal weighting functions, which transformations may not allow for physiological interpretation.

With development of more advanced dosage forms, especially for formulations that provide a delayed release of active compound, better predictive models are necessary. Thus, there was a need for an integrated assessment of the in vitro dissolution of a pharmaceutical formulation and the absorption of an active compound from such formulation, which parameters had previously been considered separately. There was also a need for an in vitro dissolution test that takes into account the absorption of the active substance by the body and the presence of dissolved active substance during the dissolution. An in vitro dissolution test that is able to demonstrate Level A IVIVC without the need for mathematical models to transform the in vitro data was also needed. Finally, an in vitro test was needed that could be used with different dosage forms of the same active ingredient that would produce Level A IVIVC for other dosage forms without the need for different test conditions for each dosage form.

To address the aforesaid shortcomings, dissolution test apparatus having at least two cells arranged in series have been developed, as described in U.S. Pat. No. 6,799,123 and U.S. Patent Application Publication Nos. 2007/0092404 and 2007/0160497. The dissolution testing systems described in these patent documents are very similar to one another. All of them have at least a first continuous flow cell and a second continuous flow cell, arranged in series. Each cell has an interior chamber through which media are passed and the media simulate various bodily fluids, such as gastric and intestinal fluids. Each cell also has a tight-fitting lid which separates the chamber from the exterior, ambient environment, which is believed to permit more accurate simulation of the digestion and absorption processes which occur in the body in vivo. The media (simulated bodily fluids) are provided to the chamber of each cell from one or more reservoirs by using pumps. A sample addition port provided in each tight-fitting lid enables the users to pass a dosage form having one or more active substances into the chamber to contact the media. One or more of the cells may have a dip tube and Tee assembly which allows for passage of media and some undissolved solids from the chamber of a particular cell to the chamber of the next downstream cell, when desired. Each of the cells is typically equipped with a stirring device to facilitate dissolution of active substance into the media inside the chamber. Various other inlets, outlets and ports are also provided for passing media and other materials to the chamber, as well as for taking samples for analysis during continuous operation of the dissolution test system, i.e., without having to open the chambers. Heating and insulating devices are also provided for controlling the temperature of the media in the chambers. Various analytical devices are provided to test for presence of active ingredients, as well as to measure the temperature and pH of the media in each chamber.

Pharmaceutical dosage forms may introduced into the cells by various manual means including, but not limited to, removal of the cover, dropping the dosage form into the chamber and replacement of the cover. As mentioned above, the apparatus described in U.S. Pat. No. 6,799,123 allows a dosage form to be added through the sample addition port, which is sealingly filled with a stopper which is removed while the dosage form is dropped in, and then replaced. Both of these manual methods of providing dosage forms to the cells require temporarily stopping the pumps, exposing the chamber to the ambient environment while the dosage form is added, and then restarting the pumps after the chamber is re-sealed.

Active substances cannot provide pharmaceutical benefits until absorbed into the tissues and blood of the body, which first requires that they be dissolved. The in vivo dissolution and absorption of active substances in the human gastro-intestinal system are understood to proceed, generally, as follows. Dissolution of the active substance may or may not begin in the mouth, which is more technically referred to as the buccal region of the gastro-intestinal system. If at least a portion of the active substance dissolves in the buccal region, then at least a portion of the dissolved active substance is likely to be absorbed into the tissues and blood proximate to the buccal region. Once past the buccal region, the active substances are not exposed to the ambient environment, but rather only to the interior conditions of each portion of the gastro-intestinal system. In vivo, some of the dissolved active substances, as well as most of the remaining solid, undissolved active substances are passed to the stomach, or gastric region, for further dissolution and absorption by the tissues and blood vessels proximate to the gastric region. From there, some of the dissolved active substances, as well as any remaining solid, undissolved active substances, pass from the gastric region into the small and large intestines, or more generally, the intestinal region, where solid, undissolved active substances are further dissolved and, hopefully, most of the dissolved active substances still present in the intestinal fluids are absorbed into the blood stream, more technically referred to, generally, as the circulatory region. However, solid, undissolved particles, if any, remaining in the intestines are not taken up by the circulatory region, but rather, they are passed down the remainder of the intestinal tract and eliminated from the body as waste.

Based on the foregoing progression of active substances through the gastro-intestinal system, in vivo, the various cells and chambers used to simulate conditions in the buccal and gastric regions (in vitro) must be capable of passing undissolved solids, up to a certain size, along with the liquid media and dissolved active substances, to chambers which simulate the gastric and intestinal regions, respectively. However, the chamber or chambers which simulate the intestinal region must be capable of retaining solid, undissolved particles, while passing media and dissolved active substances to the chamber or chambers which simulate the circulatory region. These requirements for the intestinal chambers are accomplished using a filter in the chamber at the outlet which leads to the downstream circulatory chamber, as explained in U.S. Pat. No. 6,799,123.

In U.S. Patent Application Publication Nos. 2007/0092404 and 2007/0160497, improved continuous flow dissolution test apparati, similar to that described in U.S. Pat. No. 6,799,123 are disclosed, along with methods for using them. In particular, U.S. Patent Application Publication No. 2007/0092404 describes using a filter support in the chamber of the second cell, positioned between the filter and the base (interior bottom surface) of the chamber to prevent distortion of the filter as it collects undissolved solids thereon.

On the other hand, U.S. Patent Application Publication No. 2007/0160497 discloses a sample holder device which operates with the sample addition port of the lid of a cell to enable addition and removal of a dosage form to the chamber within the same cell, during continuous operation of the multiple flow-through cell dissolution test system, without having to stop the flow of media or expose the contents of the chamber to the ambient environment. More particularly, the sample holder includes a tower removeably affixed to the lid of the cell at the sample addition port. A plunger is slidable within an interior region of the tower, between a "raised" position and an "extended" position. A basket for retaining or holding a dosage form is attached to the distal end of the plunger and is moved into and out of the chamber with the aforesaid sliding movement of the plunger. The basket is made of wire or mesh to permit media in the chamber to flow through and contact the dosage form for dissolution of active substance from the dosage form.

In operation, as described in U.S. Patent Application Publication No. 2007/0160497, prior to beginning the flow of media into the cells, the dosage form is placed in the basket of a sample holder device, the plunger is slid into the "raised" position (i.e., the basket is held above and outside the chamber of the cell) and the tower of the sample holder is removably affixed to the lid. After media is provided to the chambers and the system has reached equilibrium (i.e., the flow rates from each pump, the media volumes and pH in each chamber are within the desired ranges), the plunger may moved to its "extended" position, placing the dosage form in contact with the media in the chamber, without having to stop the media flow or expose the chamber to the ambient environment. The basket and dosage form may even be raised back out of the media during continuous operation of the flow-through system. However, the sample holder may not be removed from the lid without shutting off the flow of media and exposing the chamber and its contents to the ambient environment and, therefore, a second dosage form cannot be added for testing, nor can the original dosage form be removed from the cell entirely for inspection or insertion into a different cell in the system. This arrangement, while an improvement upon previous dissolution technology, still presents some limitations in practice.

SUMMARY OF THE INVENTION

The present invention provides a dissolution test cell for use with a continuous flow dissolution test apparatus and method in which a dosage form is contacted with media and the media is analyzed for concentration of an active substance. The dissolution test cell comprises (A) a vessel having a chamber for holding the media and dosage form therein, at least one inlet and at least one outlet, each of said at least one inlet and at least one outlet being in fluid communication with said chamber for passage of media and dissolved materials; (B) a tight-fitting lid attached to the vessel for enclosing the chamber and preventing uncontrolled fluid communication between the chamber and the ambient environment; (C) a dosage form holder; and (D) a mixing device for mixing the media, dosage form and dissolved materials in said chamber.

The lid comprises an opening for passage therethrough of a dosage form into the chamber and a slide valve which is sealingly affixed to the lid proximate the opening. The slide valve assembly itself comprises a planar member which is moveable between an open position and a closed position. In the open position, fluids and materials are permitted to pass through the opening and into the chamber and, in the closed position, fluids and materials are prevented from passing through the opening. The slide valve assembly also comprises an actuator in communication with the planar member and being externally accessible for moving the planar member between its open and closed positions during operation of said dissolution test cell.

Furthermore, the dosage form holder has a compartment and is removably and sealingly attached to said slide valve assembly. When the planar member of the slide valve assembly is in its open position, the compartment is in fluid communication with the opening and the chamber and a dosage form is permitted to pass from the compartment, through the opening of the lid, and into the chamber. In one embodiment, the planar member of the slide valve assembly has an opening therethrough which is sized and shaped to align with the opening of the lid when the planar member is in its open position, whereupon said dosage form is permitted to pass through the openings. The planar member also has a solid portion which sealingly blocks fluid communication with the opening of the lid when the planar member is in its closed position.

The slide valve may further comprise a threaded annular sleeve aligned with the opening of the lid. In another embodiment, the dosage form holder may comprise a hollow cap sized and shaped to receive a dosage form thereunder and having an annular threaded interior surface which cooperates with the annular threaded sleeve of the slide valve assembly to removably and sealingly attach the hollow cap to the sliding valve assembly.

In still another embodiment, the dosage form holder which comprises (A) a hollow tower portion having an interior cylindrical passage and an internal annular threaded surface which cooperates with the threaded sleeve of the slide valve assembly to removably and sealingly attach the sample holder device to said slide valve assembly, (B) a plunger disposed in the cylindrical passage of the tower, wherein the plunger is slidable between a raised position and an extended position, and (C) a basket attached to the distal end of the plunger for holding a dosage form. When the plunger of this sample holder device is in its raised position the basket is outside the chamber, and when the plunger is in its extended position the basket is in the chamber and in contact with media therein.

The present invention also provides a dissolution test apparatus comprising one or more cells in accordance with the dissolution test cell of the present invention.

In one embodiment, the dissolution test apparatus comprises a first dissolution test cell in accordance with the dissolution test cell of the present invention and has a first chamber which is connected in series to at least a second dissolution test cell in accordance with the dissolution test cell of the present invention and having a second chamber. In this embodiment, the first dissolution test cell is capable of transferring solid test samples to the second dissolution test cell and the second dissolution test cell is capable of retaining the solid test samples. The dissolution test apparatus may have a processor for analyzing an effluent from the chambers. The dissolution test apparatus may further comprise a first reservoir and at least a second reservoir for continuously supplying one or more media into the first chamber and the second chamber, respectively. Each chamber further has a stirrer for mixing the solid test samples and the media together. The second chamber has a filter membrane overlying a base of the second chamber.

BRIEF DESCRIPTION OF THE DRAWINGS

A more complete understanding of the present invention will be gained from the embodiments discussed hereinafter and with reference to the accompanying drawings, in which like reference numbers indicate like features, and wherein.

DETAILED DESCRIPTION OF THE INVENTION

Figure 1:
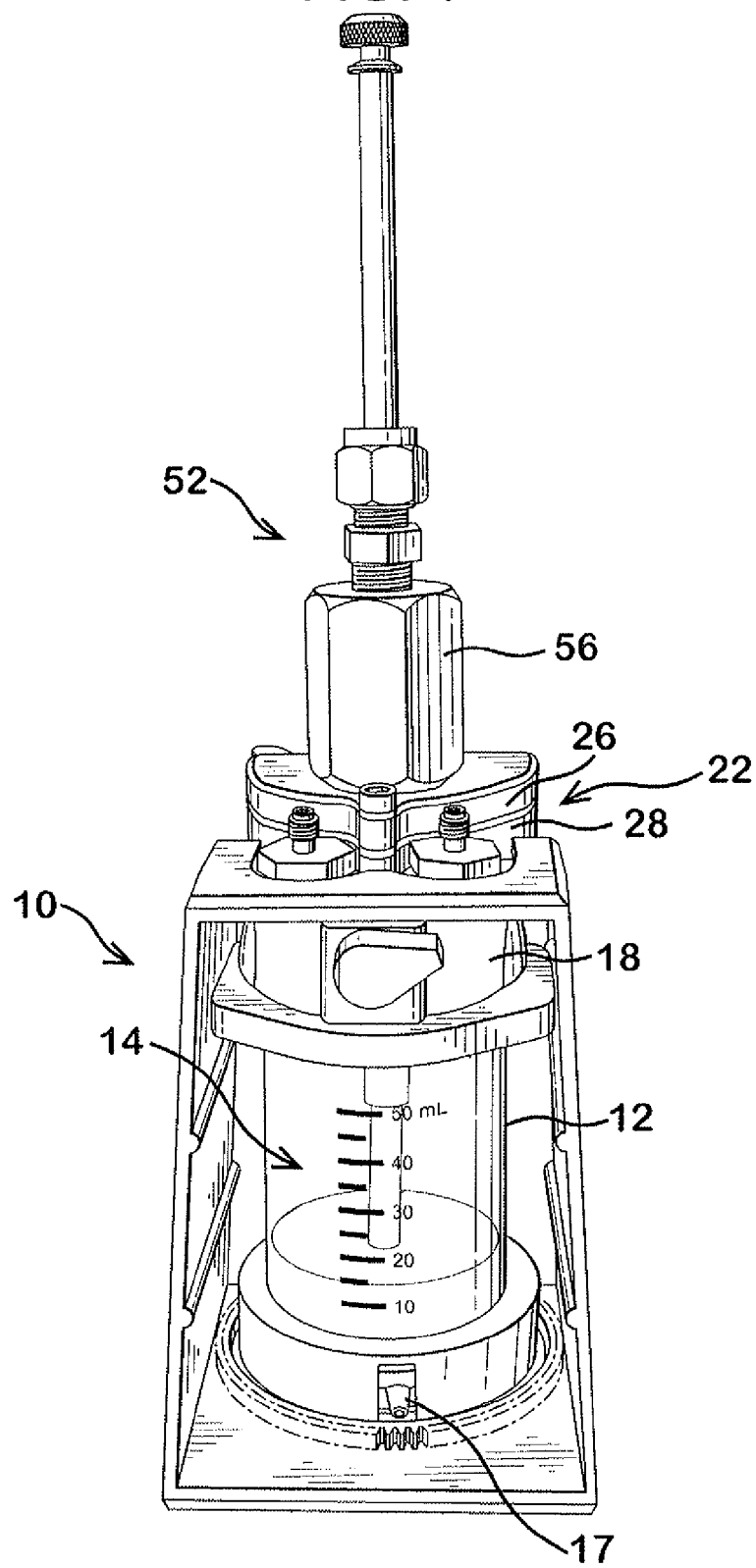
FIG. 1 is a front perspective view of the dissolution test cell in accordance with the present invention.

The present invention provides a continuous flow dissolution testing apparatus and methods for testing that allow passage of dosage forms between the ambient environment and one or more chambers of the apparatus, during continuous operation of the apparatus, i.e., without requiring interruption of the flow of media through the chambers, and without exposure of the chambers and their contents to the ambient environment. The ability to pass dosage forms between the ambient environment and one or more chambers of the apparatus during continuous operation of the apparatus provides better, more accurate test results while enabling a wider range of test conditions, including, but not limited to, retrieval, substitution, manual transfer and supplementation of dosage forms during continuous operation of the test apparatus. Moreover, the performance benefits of previously developed dissolution testing apparatus are retained including, without limitation, accomplishing the required degree of sample disintegration, solids transfer, dissolution, changing pH/composition of fluids, absorption, and clearance, as well as providing an excellent Level A IVIVC which is accurately predictive across different dosage forms of the same drug, without use of mathematical models.

The following terms have the following meanings herein:

The terms "medium", "media", or "release medium" as used herein, means the liquid medium into which a dosage form and/or active substance is being released and dissolved. Examples of release media include, without limitation, water, simulated buccal fluid (such as simulated saliva), simulated gastric fluid, simulated intestinal fluid, simulated circulatory fluid, or the authentic physiological versions of these fluids, other synthetic analogs of physiological fluids, milk-based fluids, fluids representing fed-state and fasted state physiological fluids, and various buffer solutions.

The term "residence time" as used herein, is a well known engineering concept applied to continuous flow systems, and is calculated by mathematically dividing the volume of liquid in a vessel by the flow rate into an out of the vessel such that the volume of liquid remains constant. For example, a flow rate of 5 ml/min into and out of a vessel containing 10 ml of liquid has a residence time of 2 minutes. Thus, residence time provides a measure of the time during which a material or substance of interest is exposed to the conditions (temperature, pressure, pH, etc.) existing within the interior region of the apparatus being used. The time distribution of molecules, atoms, ions etc in such systems is well understood in the engineering field and described in many Chemical Engineering texts, for example, Chemical Engineering Kinetics, $2^{nd}$ Edition, Chapter 5, Mcgraw-Hill Book Company 1970.

The term "resinate" as used herein, means the product derived from forming a complex between an ion exchange resin and an ionizable organic compound.

The term "dosage form," "sample," "composition," "agent," "compound", or "substance" as used herein, means a chemical, a material, a composition, a blend, or a mixture of materials or components that carries and releases one or more active substance. A dosage form, sample, composition, agent, compound or substance, may, without limitation, for example, be in the form of a tablet, powder, pill, syrup, fast-melt tablet, hard capsule, soft capsule, geltab, and slow release tablet or capsule. Furthermore, the terms "characteristics," "parameters," and "specifications" may be used herein interchangeably and are intended to refer to a property, ingredient, quantity, quality, etc. of the composition or dosage form under discussion.

The term "buccal chamber" as used herein, refers to a chamber of the flow-through dissolution system of the present invention that is designed and operated to simulate the in vivo conditions of a patient's mouth and upper digestive tract during ingestion and initial digestion of a dosage form, as described further hereinbelow.

The term "gastric chamber" as used herein, refers to a chamber of the flow-through dissolution system of the present invention that is designed and operated to simulate the in vivo conditions of a patient's stomach during digestion of a dosage form, as described further hereinbelow.

The term "intestinal chamber" as used herein, refers to a chamber of the flow-through dissolution system of the present invention that is designed and operated to simulate the in vivo conditions of a patient's intestine during continued digestion and absorption of a dosage form, as described further hereinbelow.

The term "circulatory chamber" as used herein, refers to a chamber of the flow-through dissolution system of the present invention that is designed and operated to simulate the in vivo conditions of a patient's blood and other circulatory fluids further absorption and delivery of the components of a dosage form, as described further hereinbelow.

The terms "release profile" and "dissolution profile" as used herein, mean the change in concentration with time of the substance being tested.

Referring now to the drawings, FIG. 1 shows a front perspective view of dissolution test cell 10 in accordance with the present invention. More particularly, the dissolution test cell 10 comprises a vessel 12 having a chamber 14 for holding media and a dosage form (not shown) therein. The vessel 12 also has at least one inlet 16 (not shown in FIG. 1, but see FIGS. 2 and 3) and at least one outlet 17, each of which are in fluid communication with the chamber 14 for passage of media and dissolved materials into and out of the chamber 14. A mixing device, such as a propeller 15 (not shown in FIG. 1, but see FIGS. 7A, 7B and 8) is also included with the dissolution test cell 10 for mixing the media, dosage form and dissolved materials in the chamber 14.

With further reference to FIG. 1, a tight-fitting lid 18 is attached to the vessel 12 to enclose the chamber 14 and prevent uncontrolled fluid communication between the chamber 14 and the ambient environment. As used herein, "ambient environment" is used to mean simply the environment surrounding and outside of the dissolution test apparatus, as compared to the interior regions and spaces of the apparatus through which media and other materials pass and flow and which form a closed system.

Figure 5:
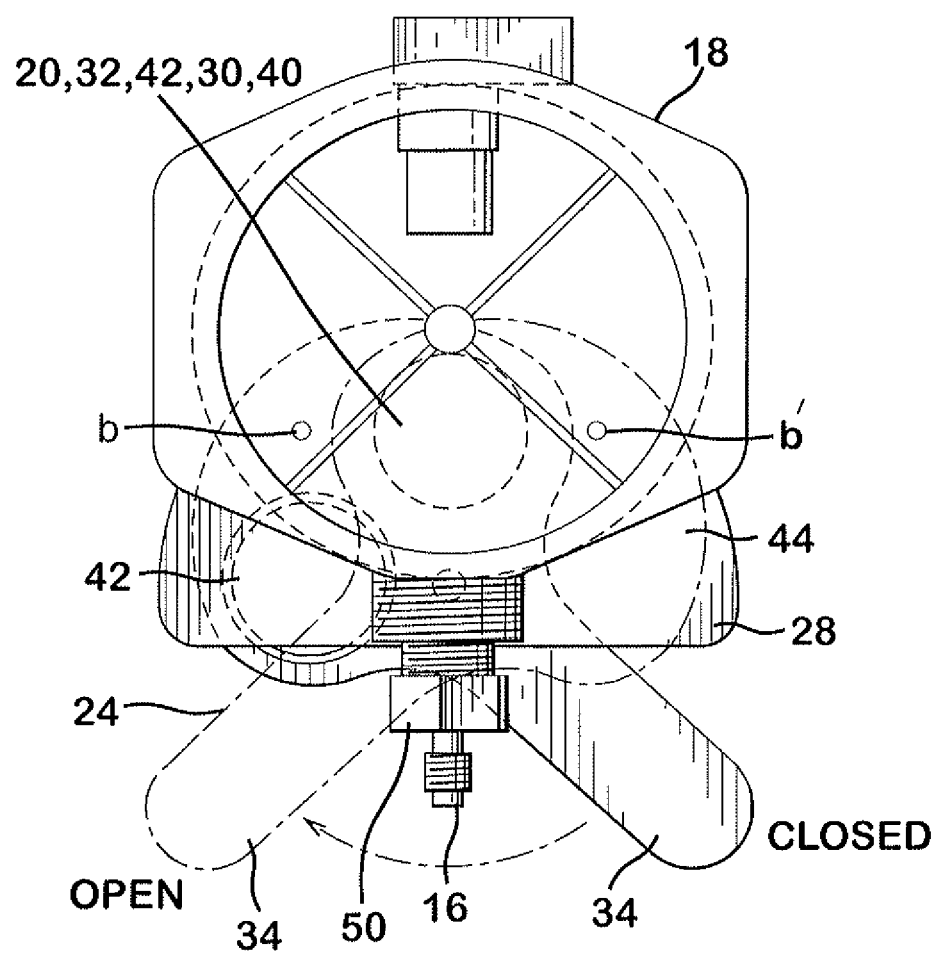
FIG. 5 is the bottom plan view of the tight fitting lid and slide valve assembly of FIG. 2, showing the open and closed positions of the planar member in the slide valve assembly.
Figure 6:
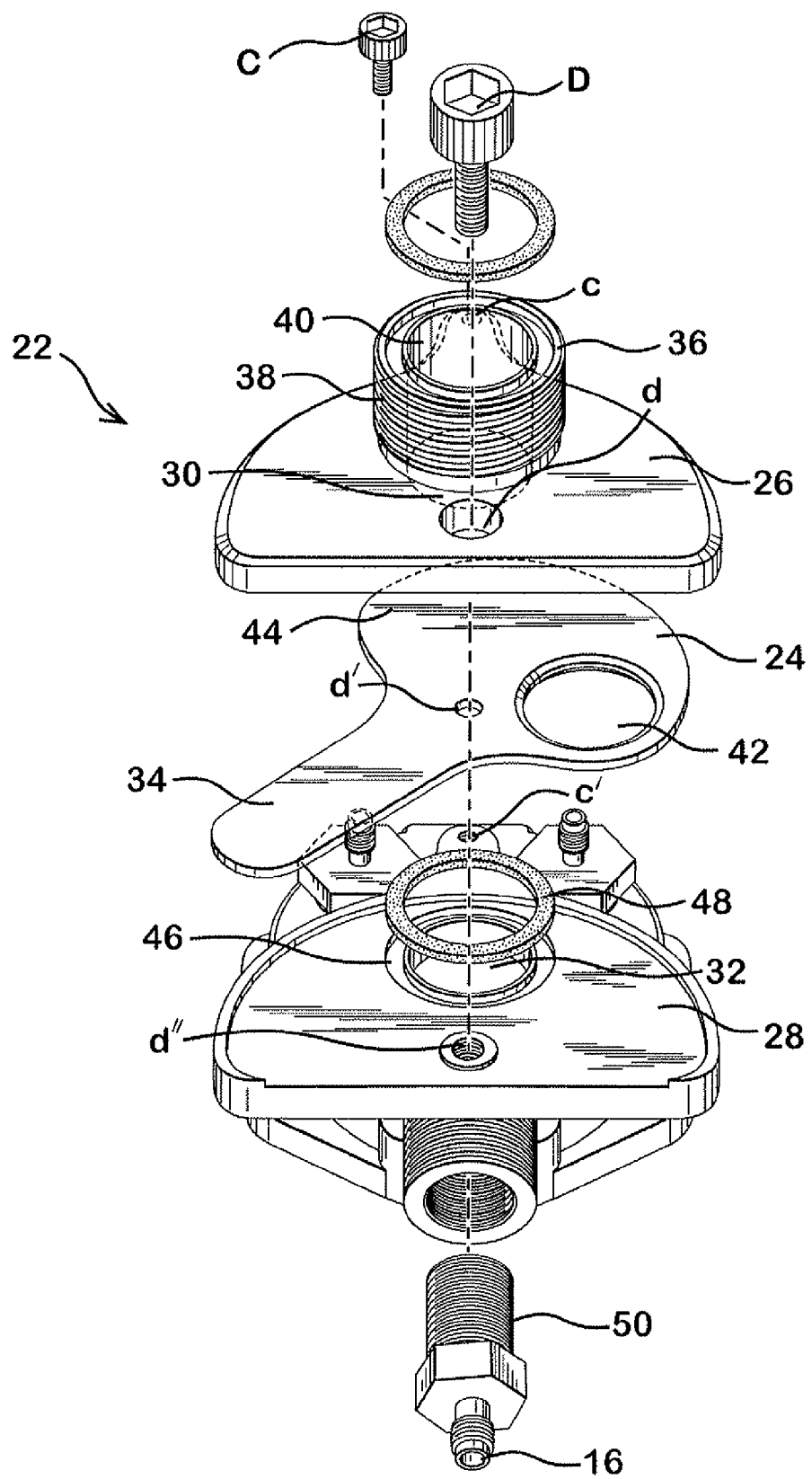
FIG. 6 is an exploded perspective view of the tight fitting lid and slide valve assembly of FIG. 2.

As shown more clearly in FIGS. 5 and 6, the lid 18 has an opening 20 (not shown in FIG. 1) for passage therethrough of a dosage form (not shown) into the chamber 14, while a slide valve assembly 22 is sealingly affixed to the lid 18 proximate the opening 20 to provide control of the passage of dosage forms and other fluids and materials into and out of the chamber 14.

Figure 2:
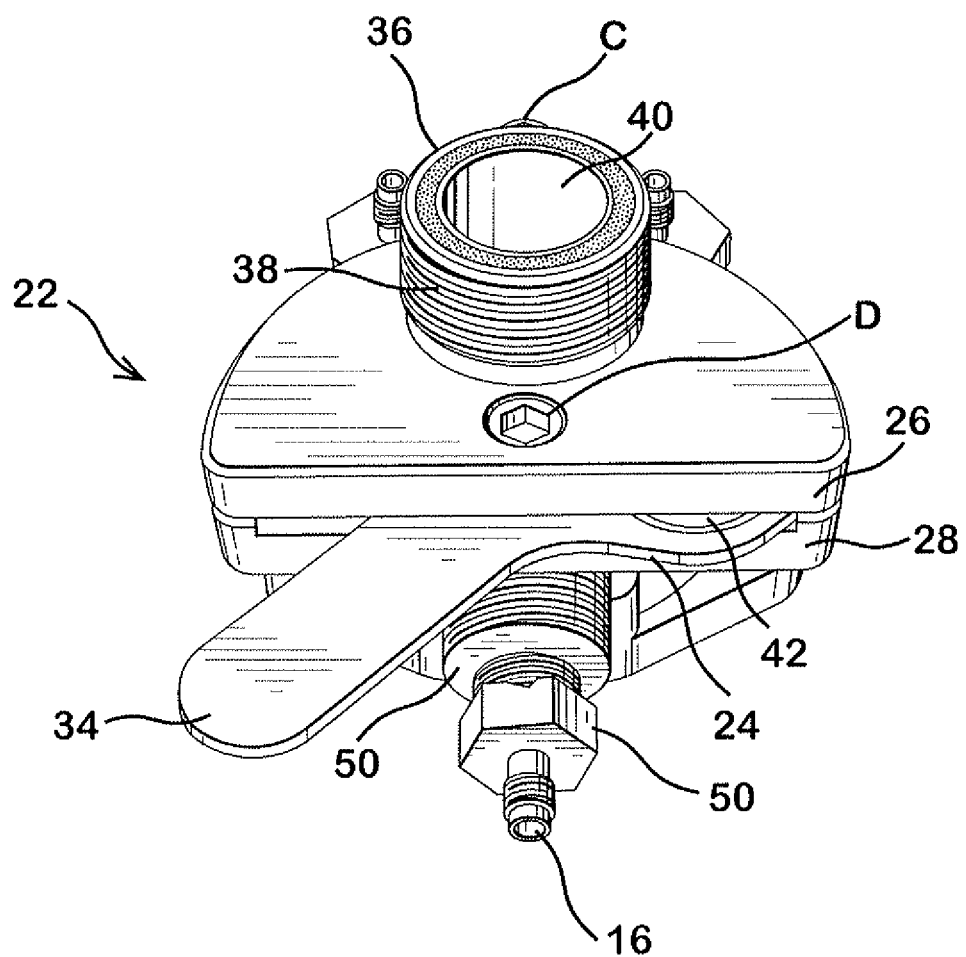
FIG. 2 is a rear perspective view of the tight-fitting lid with the slide valve assembly attached thereto.

FIGS. 2-6 provide various views of the tight-fitting lid 18 and slide valve assembly 22 to facilitate understanding of their various features and operation, as described in further detail hereinafter. In particular, FIG. 2 shows a rear perspective view of the lid 18 and slide valve 22, while FIGS. 3, 4A, 4B, 4C and 5 provide various plan views, i.e., top, front elevational, rear elevational, right side elevational, and bottom plan views, respectively. The left side elevational view of the lid 18 and slide valve 22 is a mirror image of the right side elevational plan view shown in FIG. 4C. Finally, FIG. 6 shows an exploded perspective view of the lid 18 and slide valve 22 to provide further detail concerning one particular embodiment of the present invention. With reference now to FIGS. 2-6, the slide valve assembly 22 comprises a planar member 24 (see FIGS. 2, 3, 5 and 6) which is pivotably held between a pair of plates 26, 28, each of which have an opening 30, 32 therethrough (see FIG. 6) for a purpose to be described hereinafter. The planar member 22 is moveable between an open position and a closed position. As can be seen in FIGS. 2, 3, 4C, 5 and 6, the slide valve assembly 22 may also comprise an externally-accessible actuator 34, in communication with the planar member 24, for manual movement of the planar member 24 between its open and closed positions during continuous operation of the dissolution test cell 10 (i.e., without disconnecting the lid 18 or slide valve assembly 22, and without exposing the chamber 14 and its contents). For example, as shown in FIGS. 5 and 6, the actuator 34 may simply be an extension or tab 34 which extends from the planar member 24 and out beyond the plates 26, 28.

Furthermore, the slide valve assembly 22 may include an annular sleeve 36 with external threads 38 and an axial passage 40 (see FIGS. 2 and 6) therethrough, for purposes to be made clear hereinafter. As shown in the figures, the annular sleeve 36 should be affixed to, or extend from, one of the plates 26 of the slide valve assembly 22 so as to encircle the opening 30 of the plate 26.

As seen most clearly in FIG. 6, in one embodiment, the aforesaid components of the slide valve assembly 22 are arranged and affixed to one another, and to the lid 18, by bolts and screws such that the openings 30, 32, 20 of the plates 26, 28 and lid 18, as well as the axial passage 40 of the annular sleeve 36 are aligned with one another to form a passageway completely through the lid 18 and valve assembly 22, with the planar member 22 pivotably positioned between the plates.

Figure 3:
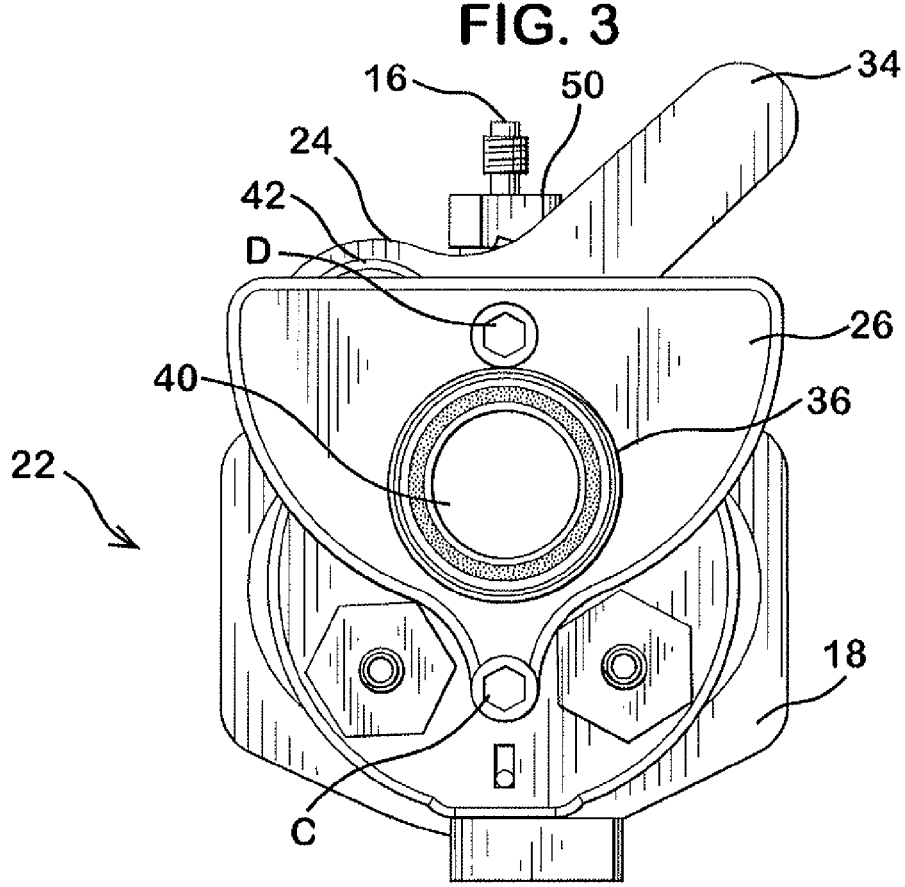
FIG. 3 is the top plan view of the tight fitting lid and slide valve assembly of FIG. 2.
Figure 4A:
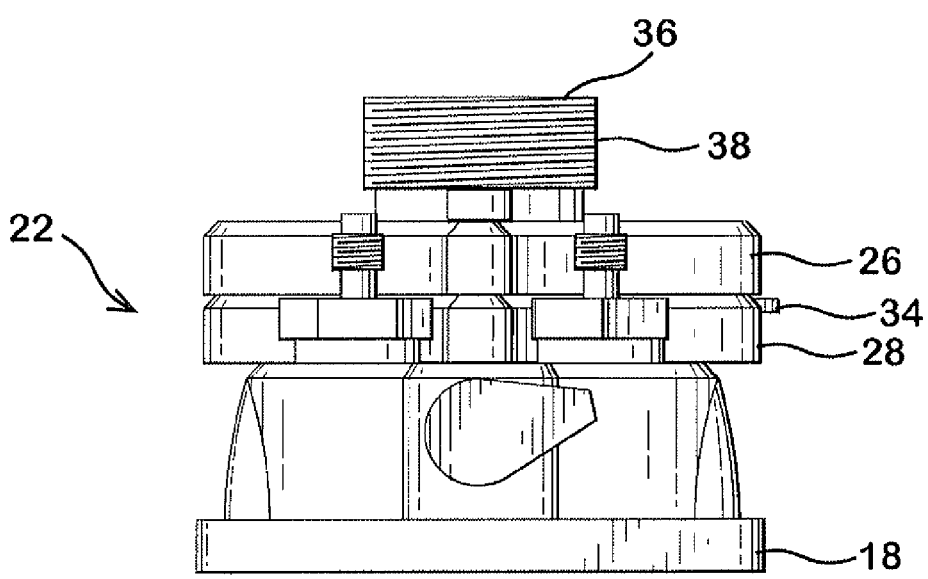
FIGS. 4A, 4B and 4C are the front elevational plan view, rear elevational plan view, and right side elevational plan view, respectively of the tight fitting lid and slide valve assembly of FIGS. 2 and 3, the left side elevational plan view being a mirror image of FIG. 4C.
Figure 4B:
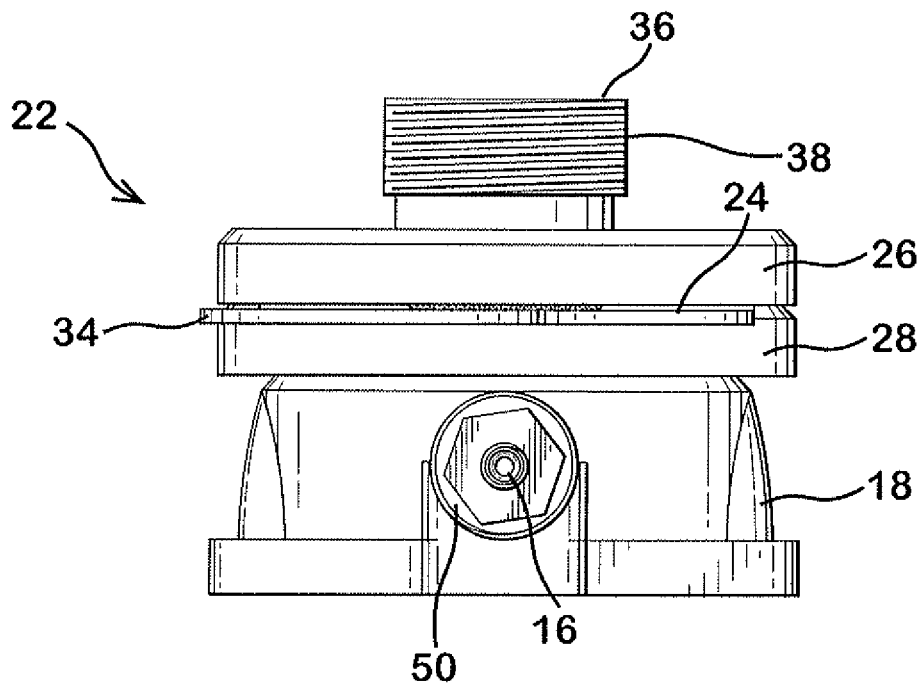
Figure 4C:
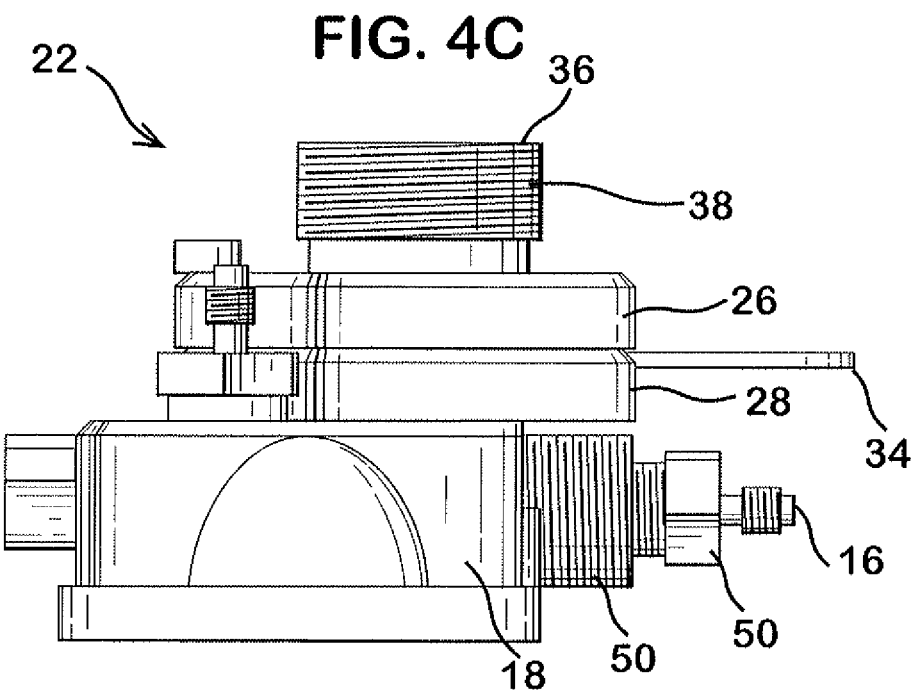

In the embodiment shown most clearly in FIGS. 5 and 6, the planar member 22 has an opening 42 therethrough which is sized and shaped to align with the passageway formed by the axial passage 40 and openings 30, 32, 20 of the annular sleeve 36, pair of plates 26, 28 and lid 18, respectively, when the planar member 24 is in its open position (see FIG. 5, OPEN). The planar member 24 also has a solid portion 44 which blocks the opening 20 of the lid 18 when the planar member 24 is in its closed position (see FIG. 5, CLOSED, entirely in phantom), whereupon fluid communication between the ambient environment and the chamber 24 is prevented. FIGS. 2, 3 and 6 also show the planar member 24 and actuator 34 in the closed position, whereby the solid portion 44 of the planar member 24 blocks the passageway.

Thus, when the planar member 24 is in its open position (OPEN, FIG. 5) as described above, dosage forms, fluids and materials (not shown) are permitted to pass through the passageway formed by the aligned openings 30, 42, 32, 20 and into the chamber 14. Alternatively, when the planar member 24 is in its closed position (CLOSED, FIG. 5), dosage forms, fluids and materials are prevented from passing through the openings 32, 20 of the plate 28 and lid 18, respectively.

As will be understood by persons of ordinary skill in the relevant art, the slide valve assembly 22 may have other features, in addition to those described above, which improve the function and efficiency of the valve assembly 22 and test cell 10. For example, there may be various holes and threaded openings through the plates 26, 28 of the valve assembly 22 and the lid 18 which align with one another to allow securing these components together and to the lid 18 with screws, nuts and bolts (see FIG. 6, e.g., openings c, c' in the plates 26, 28, as well as screw B). In the embodiment shown in the accompanying drawings, the planar member 24 is pivotably movably between the open and closed positions and, therefore, aligned holes d, d", d' are provided in each of the plates 26, 28 and planar member 24, respectively to receive a bolt D therethrough, which is the pivot point for movement of the planar member 24. Also, in FIG. 6 and in the bottom plan view shown in FIG. 5, aligned holes a', b' are provided in the lid 18 and the plate 28 of the slide valve assembly 22 adjacent to the lid 18 for insertion of screws to secure the slide valve assembly 22 to the lid 18.

Additionally, one of the plates 28 may have a raised edge 46, as shown in FIG. 6, to provide space for the planar member 24 to fit in between the plates 26, 28 when they are sealingly fastened together. To create a fluid-tight seal around the openings 30, 32 of the plates 26, 28, while still allowing sliding movement of the planar member 24 therebetween, each plate 26, 28 may have an annular recess surrounding the opening which receives a rubber gasket. For example, in FIG. 6, one plate 28 is shown having an annular recess 46 around the opening 32 and a gasket 48. The gasket 48 fits snugly within the recess 46, protruding slightly therefrom, to contact the surface of the planar member 24 and provide a fluid-tight seal about the aligned openings 32, 42 of the plate 28 and planar member 24. There may be a mirror image recess-and-gasket arrangement surrounding the opening 30 of the other plate 26, which is not visible in FIG. 6.

The lid 18 may have an opening (not visible in FIG. 1) and apparatus 50 connected thereto for forming the inlet 16 (see FIGS. 2, 3, etc.) which is in fluid communication with the chamber 14 when the lid 18 is sealingly affixed to the vessel 12. Tubes, hoses, conduits, etc. may be sealingly fastened to the apparatus 50 to provide fluids to the chamber 14 through the inlet 16 during operation of the dissolution test cell 10.

With reference briefly to FIGS. 1, 7A, 7B and 8, the dissolution test cell 10 of the present invention further comprises a dosage form holder 52 which has a compartment 53 therein for receiving a dosage form (not shown). The dosage form holder 52 should sealingly and removably attached to the slide valve assembly 22. For example, without limitation, the dosage form holder 52 may have an annular threaded portion which cooperates with the threaded annular sleeve 36 of the slide valve assembly 22, as described in further detail hereinafter. When the planar member 24 of the slide valve assembly 22 is in its open position, the compartment 53 of the dosage form holder 52 will be in fluid communication with the chamber 14, through the above described passageway (formed by the axial passage 40 and openings 30, 32, 20 of the annular sleeve 36, pair of plates 26, 28 and lid 18), whereupon a dosage form (not shown) will be permitted to pass from the compartment 53 of the dosage form holder 52, through the opening 20 of the lid 18, and into the chamber 14.

In one embodiment, for example, without limitation, the dosage form holder 52 may be a plunger and basket assembly 54, such as that described briefly hereinabove and in detail in U.S. Patent Application Publication No. 2007/0160497. More particularly, with reference to FIGS. 7A and 7B, the plunger and basket assembly 54 comprises a hollow tower portion 56 with an interior cylindrical passage 58 having an internal annular threaded surface (not shown) and providing the aforesaid compartment 53. The internal annular threaded surface (not shown) cooperates with the threaded sleeve 36 of the slide valve assembly 22 to sealingly and removably attach the plunger and basket assembly 54 to the slide valve assembly 22 (see FIG. 1).

Figure 7A:
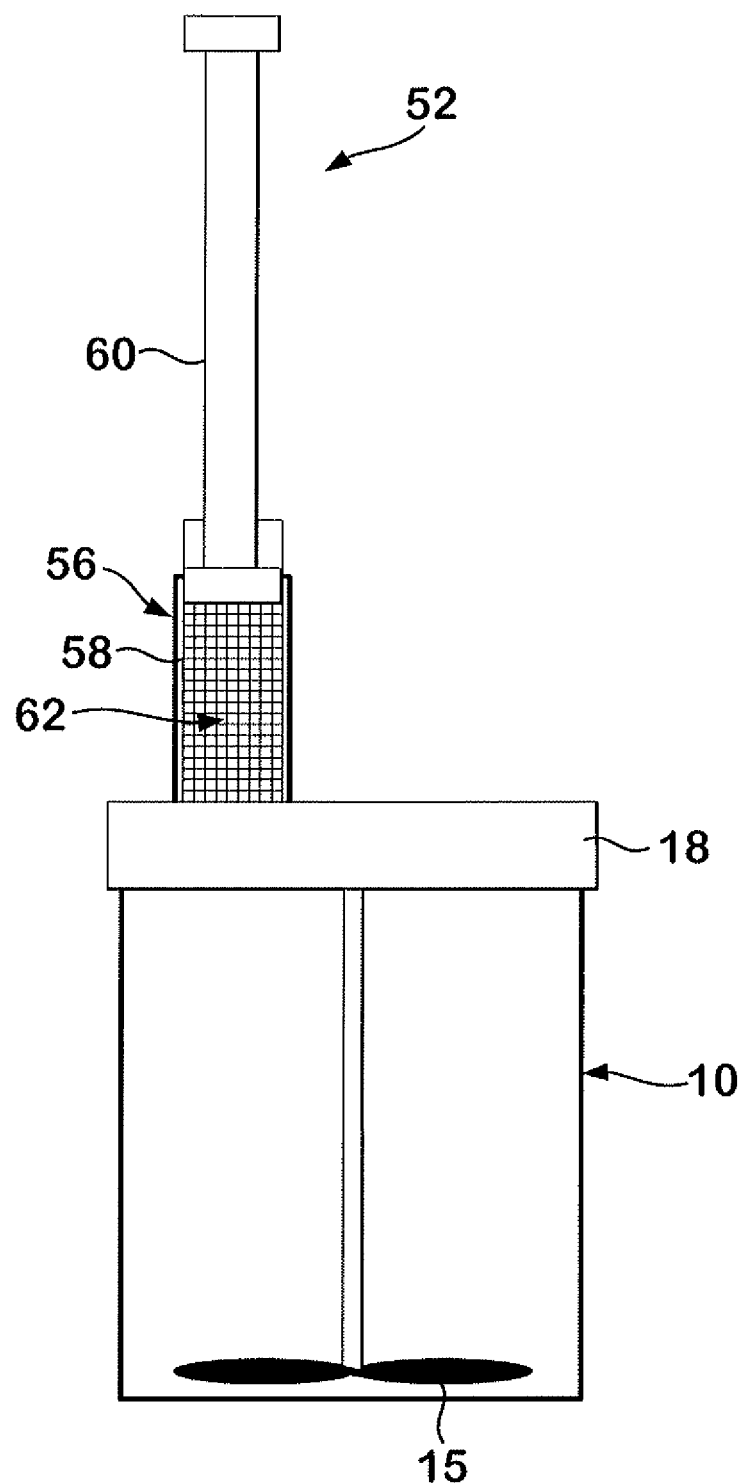
FIGS. 7A and 7B are simplified schematic left side elevational views of a vessel and one embodiment of a dosage form holder having a plunger and basket in a raised position and an extended position, respectively (slide valve assembly omitted)
Figure 7B:
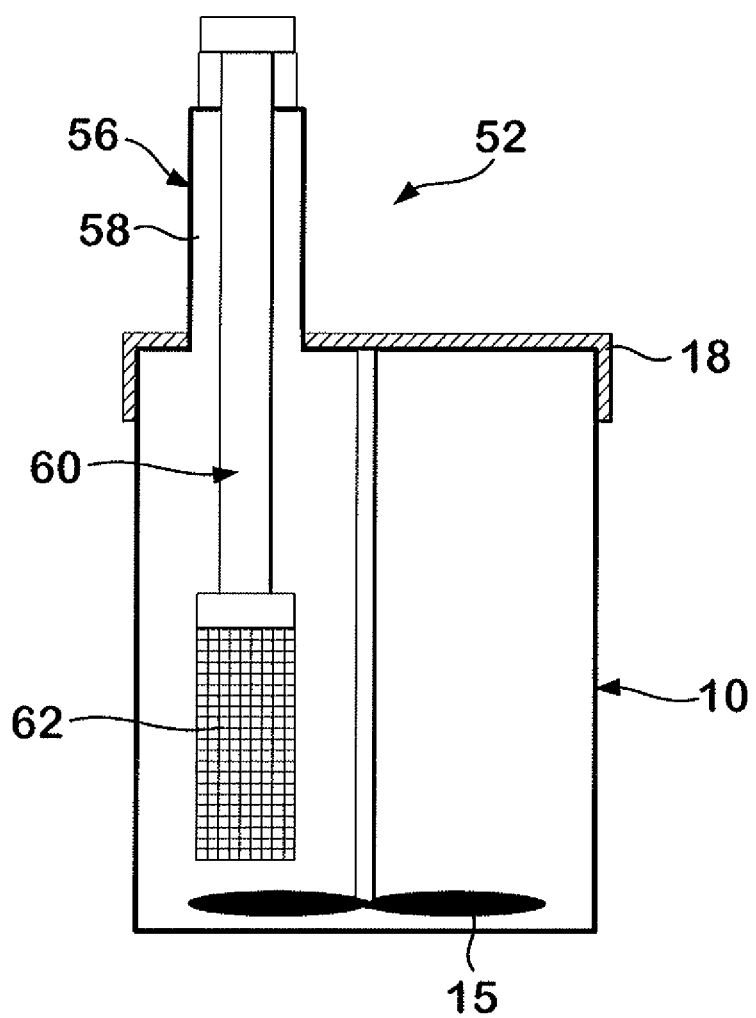

The plunger and basket assembly 54 further comprises a plunger 60 disposed in the cylindrical passage 58 of the tower 56 and is slidable between a raised position and an extended position (see FIGS. 7A and 7B, respectively). A basket 62 is attached to the end of the plunger 60 for holding a dosage form (not shown). When the plunger 60 is in its raised position (FIG. 7A) the basket 62 is positioned within the compartment 53 and outside the chamber 14 and, thus, is not in contact with the media (not shown) in the chamber 14. Alternatively, when the plunger 60 is in its extended position (FIG. 7B) it extends through the compartment 53 and the basket 62 is positioned in the chamber 14, which places the dosage form (not shown) in contact with media (not shown) in the chamber 14.

In another embodiment, not shown in the figures, the dosage form holder may be a hollow cap which is sized and shaped to receive a dosage form in a compartment thereunder and has an annular threaded interior surface which cooperates with the annular threaded sleeve 36 of the slide valve assembly 22 for removably and sealingly attaching the hollow cap to the sliding valve assembly 22.

Figure 8:
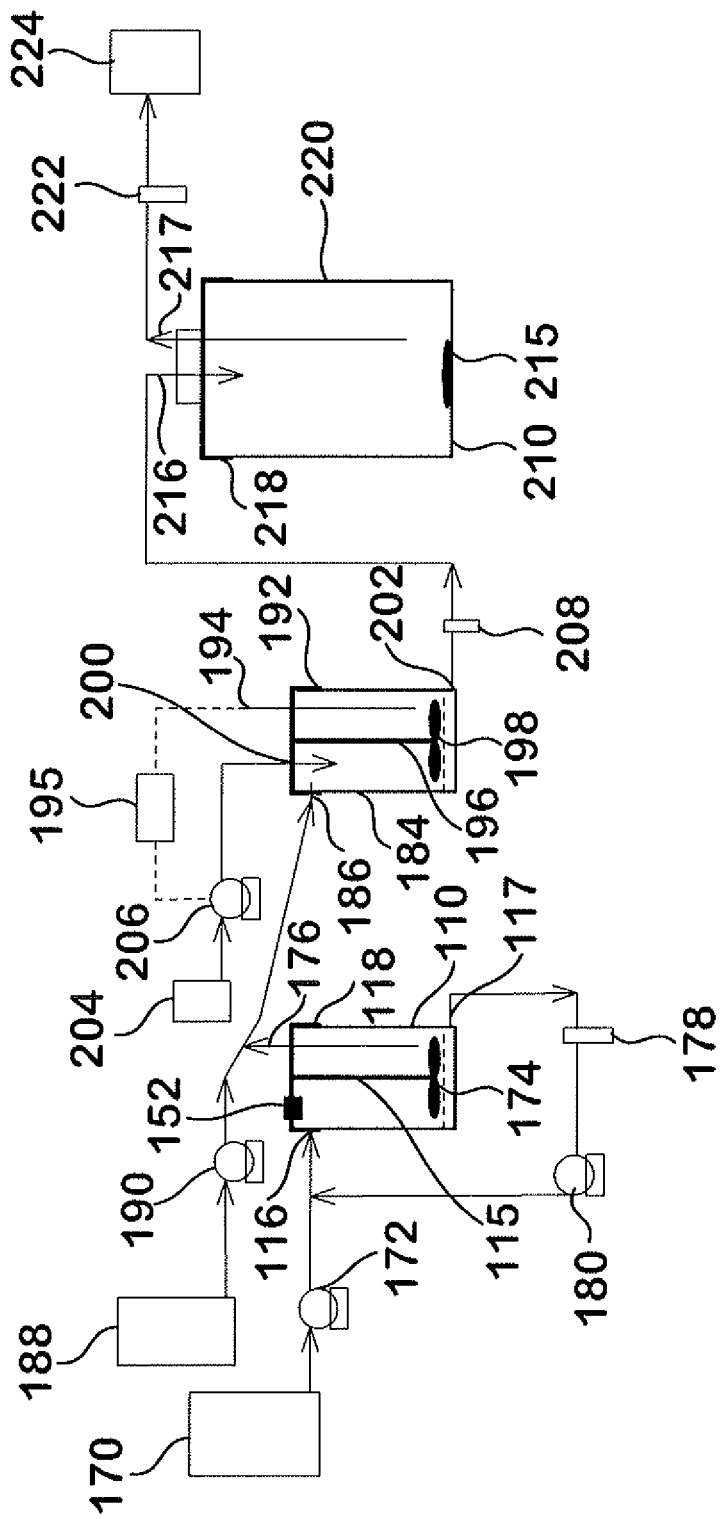
FIG. 8 is a schematic representation of a dissolution test apparatus which includes at least one dissolution test cell in accordance with the present invention.

FIG. 8 provides a schematic representation of one embodiment of a dissolution test apparatus which comprises at least one dissolution test cell in accordance with the present invention as described hereinabove. While the dissolution test apparatus shown in FIG. 8 and described in detail below is similar to that described in U.S. Patent Application Publication No. 2007/0160497, it should be understood the dissolution test cell of the present invention, which includes a slide valve assembly as described above, is not limited to use with dissolution test apparatus of the particular kind described in U.S. Patent Application Publication No. 2007/0160497. Rather, as persons of ordinary skill will readily recognize, the dissolution test cell of the present invention may be useful with any dissolution test apparatus which is used for testing the dissolution and absorption of pharmaceutically active substances, with or without various dosages forms.

With reference back to FIG. 8, a reservoir 170, a pump 172, and a first cell 110 comprising a dissolution test cell in accordance with the present invention are connected such that at least a portion of the liquid contents (media, not shown) of the reservoir 170 are transferred into the first cell 110 via the pump 172. The cell 110 is equipped with a tight fitting lid 118, a filtration membrane 174, a stirrer 115, an inlet 116, an outlet 117 positioned to allow removal of filtered liquid. The first cell 110 further comprises a dosage form holder 152, and a dip-tube and Tee assembly 176.

The dosage form holder 152 is affixed to the lid 118 of the first cell 110. The outlet 117 is connected to a flow-thru uv analyzer 178 and pump 180, such that the filtrate is pumped through the uv analyzer 178 and returned to the inlet 116 of the first cell 110. One branch of the dip-tube and Tee assembly 176 comprises a dip-tube to allow removal of liquid and small particle sized solids from the first cell 110. The second branch of the dip tube and Tee assembly 176 is connected to the outlet of a pump 182. The third branch of the dip-tube and Tee assembly 176 is connected to the inlet 186 of a second cell 184.

A reservoir 188 is connected to the pump 190 such that the liquid media from the reservoir 188 is fed into the second branch of the dip-tube and Tee assembly 176. The second cell 184 is equipped with a tight fitting lid 192, a pH sensor 194, a stirrer 196, a filtration membrane 198, two inlets 186, 200, and an outlet 202 positioned to allow removal of filtered liquid. A reservoir 204 is connected to a pump 206 and to one of the inlets 200 of the second cell 184, such that liquid from the reservoir 204 is transferred into the second cell 184. The outlet 202 is connected to a flow-thru uv analyzer 208. The outlet of the uv analyzer 208 is connected to the inlet 216 of a third cell 210. The pH sensor 194 may be electrically connected to a pH controller 195. The power supply to pump 206 is connected to the output relay of the pH controller 195 such that the pump 206 is turned on when the pH, as measured by the pH sensor 194, is below a target value, and is turned off when the pH is above a target value.

The third cell 210 is equipped with a tight fitting lid 218, a stirrer 215, a dip-tube 212, and an outlet 217. The outlet 217 is connected to the inlet of a flow-thru uv analyzer 220. The outlet from the uv analyzer 220 is directed to waste or any suitable reservoir 222.

In the embodiment shown figuratively in FIG. 8 and described here, the first cell 110 and immediately associated equipment represents a gastric chamber 110 of a human body; the second cell 184 and immediately associated equipment represents an intestinal chamber 184 of the same body; and the third cell 210 and immediately associated equipment represents a circulatory chamber 210 of the same body. Each of the flow-thru uv analyzers 178, 208, 220 is placed in a suitable uv spectrophotometer capable of measuring the absorbance of the cell contents at the desired wavelength. When control of the temperature is required any or all of the three cells 110, 184, 210 can be immersed in a suitable heating bath or a recirculating hot air oven.

In the presently described embodiment, the reservoir 170 associated with the gastric chamber 110 is filled with simulated gastric fluid, the reservoir 188 associated with the intestinal chamber 184 is filled with simulated intestinal fluid, and the reservoir 204 (also associated with the intestinal chamber 184) is filled with 0.8M aqueous sodium hydroxide solution. To start a test, the pumps 172, 180, 190, 206 are operated to fill each of the chambers/cells 110, 184, 210 to the desired volumes from the associated reservoirs 170, 188, 204 as described above, and then run for sufficient time to also fill the circulatory chamber 210, establish that the flow rate from each pump is as desired and verify that the pH of the first chamber 110 is maintained within the target range. The uv analyzers 178, 208, 220 are checked to make sure that they contain no air bubbles.

In operation, a dosage form (not shown) in the dosage form holder 152 is lowered into the first cell 110 using the plunger, down to a fixed distance within the cell 110 (see, e.g., FIG. 7B). Use of the dissolution test cell of the present invention for the first cell/gastric chamber 110 permits introduction of the dosage form (not shown) into the gastric chamber 110 without stopping/starting the pumps and without having to expose the media and active ingredient from the dosage form to the ambient atmosphere.

Exposure to the fluid in the gastric chamber causes the dosage form to be partially or completely disintegrated, or dispersed or dissolved, thereby releasing active substance, as well as excipient materials, carrier materials, etc., into the media. The dissolved portion(s) of the dosage form exits the gastric chamber 110, via the dip-tune and Tee assembly 176, together with small particles of undissolved active substance and/or excipient. Dissolved active substance and/or dissolved excipient also exits the gastric chamber 110 through the outlet 117. The filter membrane 174 prevents undissolved particles from exiting through the outlet 117. The liquid that exits though outlet 117 passes through the uv analyzer 178, where the liquid's uv absorbance at any desired wavelength is continuously monitored. The liquid is continuously returned to the gastric chamber by the pump 180, via the inlet 116. The material exiting via the dip-tube and Tee assembly 176 flows through the Tee portion thereof, where it mixes with simulated intestinal fluid delivered from the reservoir 188 by the pump 190. This mixture then enters the simulated intestinal chamber 184 via the inlet 186.

In the intestinal chamber 184, the incoming mixture is mixed with the contents of the intestinal chamber 184, together with sodium hydroxide solution entering from reservoir 204 by pump 206. Because the sodium hydroxide flow is controlled by the pH of the contents of the intestinal chamber 184, the result is that the acid present in the incoming mixture (from the gastric fluid from the gastric chamber 110) is neutralized in the intestinal chamber 184. In the intestinal chamber 184, the undissolved portion of the incoming mixture has further opportunity to dissolve. Dissolved active substance and/or dissolved excipient exits the intestinal chamber 184 through the outlet 202. The filter membrane 198 prevents any undissolved active substance and/or undissolved excipient from unintentionally exiting the intestinal chamber 184. The liquid exits though outlet 202 passes through the uv analyzer 208, where its uv absorbance at any desired wavelength is continuously monitored. The liquid exiting the uv analyzer 208 then enters the circulatory chamber 210 via the inlet 216.

In the circulatory chamber 210 the incoming medium is mixed with the medium already present in the circulatory chamber 210. The resulting mixture continuously exits the circulatory chamber 210 via the dip-tube 220 and outlet 217. The liquid that exits though outlet 217 passes through the uv cell 222, where the uv absorbance at any desired wavelength is continuously monitored. The data collected from the spectrophotometer can be used to calculate the instantaneous concentration of the active substance. The data can also be used to characterize the release rate and the total amount of active substance released. Measuring the concentration of active substance in the effluent collected in the collection reservoir 224 permits the calculation of the total amount of active substance released.

While the embodiment of the invention described above uses constant composition of media (release fluids), the compositions can be changed with time to simulate changing conditions within the body. Test method variables are, for example, composition of release media, residence time in each of the three chambers, amount of the sample being tested, and temperature. By adjusting these variables it is possible to obtain a release rate profile that matches the plasma concentration profile observed in vivo. When practiced in the pharmaceutical industry, the preferred temperature is 37° C., and the preferred composition of the release media are simulated gastric and simulated intestinal fluids.

Also, other additives, such as enzymes, bile acids, and surfactants, can be included, as desired. In addition, although the USFDA recommends that dissolution conditions be physiologically relevant, the present invention can be adapted for conditions that are not physiologically relevant. Such conditions may be desirable when considerations such as speed of operation, unusual solubility, or non conventional dosage forms are taken into account. For example, applicant has determined in some cases that by proportionally reducing residence times, the time scale of the test can be considerably shortened without loss of useful information. In addition, the invention can be used to test many different types of formulations, or dosage forms. These can include, but are not restricted to, tablets, powders, pills, syrups, fast-melt tablets, hard capsules and soft capsules.

The medium analysis device includes, but is not limited to, any detector known in the art that generates physical and/or chemical data of a pharmaceutical or active test agent, e.g., the use of a UV spectrophotometer as the method of analysis. In a preferred embodiment, the detector is capable of acquiring data characteristic of a particular agent by any method, including, ultraviolet radiation, infrared radiation, nuclear magnetic resonance, Ramen spectroscopy, electrochemical, biosensors, refractometry, optical activity, and combinations thereof. Also, any in-line detector known in the art that is applicable to the active substance and release medium can be used. Preferably, the medium dissolution analysis device is a detector that has a sensor communicatively attached thereto. In the preferred embodiment, there is at least one medium dissolution analysis device per dissolution chamber. For example, for each sample to be analyzed there is a corresponding medium dissolution analysis device capable of continuously generating physical and/or chemical data characteristic of the agent to be analyzed.

The medium analysis device preferably includes a detector operatively associated with the dissolution medium for at least the time period required for the dosage form to release the maximum releasable quantity of therapeutically active agent and a data processor for continually processing the generated data for at least the time period required for the dosage form to release the maximum releasable quantity of therapeutically active agent to obtain a dissolution profile of the dosage form. The data processor may be any device capable of continuously processing the data generated by the detector. In a preferred embodiment, the data processor is a computer. The data generated by the detector is preferably stored and/or analyzed by the computer. In a particularly preferred embodiment, the data collector is a computer that has data processing software. The data is preferably continuously processed by the software as it is received from the detector.

In the preferred embodiment of the present invention, the detector measures the concentration of the therapeutically active agent in the media surrounding the dosage form such as in simulated gastric or intestinal fluid. By measuring the concentration of the agent in the surrounding media, the amount of agent released from the dosage form can be calculated. The invention can also be used by removing samples from the chambers directly or from the effluent discharge of the chambers instead of, or in addition to in-line analysis. In such an embodiment the analytical methods can be any method known in the art, including but not limited to, Gas chromatography, liquid chromatography, high performance liquid chromatography (HPLC), colorimetry, uv spectroscopy, IR spectroscopy, Raman spectroscopy, near IR spectroscopy, bio-sensors, electrochemical methods, mass spectroscopy, and nuclear magnetic spectroscopy. In the most preferred embodiment the medium analysis is performed in-line using uv spectroscopy.

One or both of the first and second test cells 110 and 184 may be designed in accordance with the dissolution test cell of the present invention described above. For example, Amicon stirred ultrafiltration cell models 8003, 8010, 8050, 8200, and 8400, commercially available from Millipore Corporation of Billerica, Mass., U.S.A. and modified to include a tight-fitting lid and slide valve assembly in accordance with the present invention, are suitable for use in the dissolution test apparatus of the present invention.

The third cell 210 can be of any design that provides the requirements of agitation, desired volume, and compatibility with the active substance and the release media. The pumps useful in the practice of the dissolution test apparatus of the present invention can be any pump capable of attaining the desired flow rate and maintaining the flow rate constant throughout the test. These include, but are not limited to, general purpose positive displacement pumps, peristaltic pumps, diaphragm pumps, HPLC quality positive displacement pumps, syringe pumps and centrifugal pumps. Particularly suitable pumps are peristaltic pumps, diaphragm pumps, and HPLC quality positive displacement pumps. Most suitable are peristaltic pumps and HPLC quality positive displacement pumps.

Heating devices useful in the practice of the dissolution test apparatus of the present invention can be any of those known in the art that give sufficiently uniform and accurate temperature control. A suitable heating device will be able to control the temperature to within +/−2° C. of the desired temperature. A more suitable heating device will be able to control the temperature to within +/−1° C. of the desired temperature. Particularly suitable heating devices are those which are able to control the temperature in conformity with the most current recommendations in the US Pharmacopeia and like sources.

The medium analysis sensor and controller used with the intestinal chamber 184 can be any combination of sensor and controller that measures and permits control of physical characteristics such as, but not limited to, pH, osmolarity, conductivity, and concentration of specific ions. The preferred medium analysis sensor and controller are any pH sensor and pH controller available in the art that permit the control of the pH in the intestinal chamber 184 to within the target range. The most suitable medium analysis sensor and controller are any pH sensors and pH controllers available in the art that has an accuracy of +/−0.02 pH units.

In one embodiment of the present invention, the pH in the second cell 184 is controlled to the same value as that of the simulated intestinal fluid. Also, the pH in the cell 184 may be any value achievable by addition of either an acid or a base through the delivery system defined by the reservoir 204, the pump 206, and the inlet 200, and is not limited to the pH of the fluid in the reservoir 188. The solution used to adjust the pH of the second cell 184 can be acidic or basic. A suitable concentration of acid or base in the solution is one that requires a flow rate of the solution in the reservoir 204 to be not more than 10% of the total flow of the other release media. The most suitable concentration of acid or base in the solution is one that requires a flow rate of the solution to be not more than 2% of the total flow of the other release media.

The number of cells used in the equipment can be varied depending on the information required. Three cells, as described in one embodiment above, is the preferred number when correlation with blood plasma concentration data is required. When drug absorption rate data is required it is only necessary to operate the combination of gastric and intestinal chambers. A further possibility is to add a buccal cell before the gastric chamber (i.e., first cell 110) such that the effluent from the buccal dissolution chamber enters an inlet in the gastric chamber. The buccal cell would simulate a buccal chamber having conditions correlating to in vivo conditions in the human mouth. Addition of a buccal cell may be used for either drug absorption or blood plasma concentration data.

In addition, filter membranes useful in the practice of this invention can be any of the commercially available filter membranes that are compatible with the release media. Suitable filter membranes have a nominal particle size cut-off of not more than 10 microns. The more suitable filters have a nominal particle size cut-off of 0.25-5 microns. The most suitable filter membranes have a nominal particle size cut-off of 1-3 microns.

Residence times in each of the chambers useful in the practice of this invention can be any value required to give a Level A IVIVC. The preferred residence times are those that have physiological relevance. The Applicants have determined by experimentation that the following ranges of residence times are useful: gastric chamber, 5-60 minutes; intestinal chamber, 1-90 minutes; circulatory chamber, greater than 30 minutes. In addition, various other mechanical, electrical and electronic equipment may be incorporated into the present invention. For example, the equipment includes, but is not limited to, pressure relief valves, check valves, pressure relief piping, pressure control systems, surge suppressors, surge tanks, de-aerators, electronic flow control systems, proportional control systems, pressure gauges, heat exchanges (to preheat media) and flow gauges.

Accordingly, the present invention provides a new dissolution testing apparatus and methods for testing that incorporate disintegration, solids transfer, dissolution, changing pH/composition of fluids, absorption, and clearance. The present invention provides excellent Level A IVIVC and appears to be predictive across different dosage forms of the same drug. In addition, no mathematical model is required. Also, the present invention allows sample introduction and testing without interruption of the system equilibrium. The data from the testing apparatus is directly comparable to blood plasma concentration-time profiles.

EXAMPLES

Comparative Example 1

Dosage Form Holder Had Plunger and Basket, No Slide Valve

The dissolution equipment was set up with the following conditions using a 20 mesh basket, as described in US20070160497(A1). Simulated Gastric Fluid (SGF) and Simulated Intestinal Fluid (SIF, pH 6.8) were prepared according to the US Pharmacopoeia 30.

| | |
|---|---|
| SGF flow to Cell 1 | 2.50 ml/min |
| SIF flow to Cell 2 | 7.35 ml/min |
| pH of Cell 2 | 6.8 |
| Cell 1 volume | 50 ml |
| Cell 2 volume | 150 ml |
| Cell 3 volume | 1600 ml |
| Temperature | 37° C. |

One half of a 200 mg Advil tablet was placed in the basket. (A whole Advil tablet was too large to fit in the basket.) The plunger/basket was placed in its raised position. When conditions of temperature, pH, and flow rates were steady and at targeted values the basket was introduced into the fluid in the first cell by pushing the plunger to its lowered position. The tablet disintegrated in the basket, but the disintegrated solids did not leave the basket and therefore no solids transfer occurred. Based on observation, it appeared that the particle size of the disintegrated solid was too large to pass through the screen which formed the basket. Efficient solids transfer is an essential part of the test procedure, so this apparatus and method was unacceptable.

Comparative Example 2

Dosage Form Holder Had Plunger and Coil, No Slide Valve

Example 1 was repeated except that the basket was replaced with a coil of steel wire arranged to hold a whole 200 mg Advil tablet, and the test repeated as described. When the tablet was introduced into the fluid in the first cell the tablet disintegrated but the disintegrated solids interfered with the stirrer blade and stopped it. Efficient mixing is an essential part of the test procedure, so this apparatus and method were unacceptable.

Comparative Example 3

Dosage Form Holder Had Plunger with a Coil, Chamber Had a Screen Shelf Above Stirrer, No Slide Valve Example 2 was repeated except that a shelf screen (20 mesh) was used in the chamber of the dissolution cell. When the tablet was introduced into the fluid it disintegrated and the disintegrated solids transferred completely to the second cell. The stirrer continued operating. This example demonstrates that the shelf screen solves the problem of solids transfer and mixing for disintegrating dosage forms.

Example 1

Dosage Form Holder was a Cap, Chamber Had a Screen Shelf Above Stirrer, Lid Had Slide Valve In this example both a shelf screen and the slider valve of the current invention were installed on Cell 1 of a system having two cells (Cell 1 and Cell 2). Water was used as a surrogate for both SGF and SIF. No pH control was used. The test was set with the following conditions.

| | |
|---|---|
| Water flow to Cell 1 | 3.0 ml/min |
| Water flow to Cell 2 | 6.0 ml/min |
| Cell 1 volume | 70 ml |
| Cell 2 volume | 190 ml |
| Cell 3 volume | 500 ml |
| Temperature | Ambient |

With the slider valve in closed position, approx ¼ of a tablet of brilliant blue dye (Presto Dye, "Trace-a-Leak") was placed in the slider valve and the cap screwed into place. Brilliant blue dye was selected for this example to permit observation of disintegration and dissolution. When the flow rates were steady and at targeted values the slider valve was opened fully. The tablet dropped into the fluid and came to rest on the screen shelf where it disintegrated. Dissolved dye, undissolved dye, and insoluble excipients transferred completely to the second cell. The stirrer continued to operate without interruption. This example demonstrates that the slider valve/screen shelf combination permits addition of a disintegrating tablet into Cell 1 without the use of a basket and without requiring the flows to be stopped or requiring the cell to be opened.

Example 2

Dosage Form Holder has Plunger with 20 Mesh Basket, Lid has a Slide Valve, Non-Disintegrating Dosage Form In this example, the dissolution system has Cell 1 (gastric chamber) and Cell 2 (intestinal chamber) and is set up with slider valve assemblies on both Cell 1 and Cell 2. The slider valve assembly on Cell 1 is further fitted with a 20 mesh basket tablet holder at the end of the plunger rod. A 10 mg OxyContin™ tablet, a non-disintegrating extended release dosage form of oxycodone, is placed in the basket. The plunger/basket is moved to the raised position and the slider valve is closed. The slider valve of Cell 2 is in its closed position. The equipment is then started operating at the following conditions:

| | |
|---|---|
| SGF flow to Cell 1 | 1.5 ml/min |
| SIF flow to Cell 2 | 3.5 ml/min |
| pH of Cell 2 | 6.8 |
| Cell 1 volume | 60 ml |
| Cell 2 volume | 180 ml |
| Cell 3 volume | 1000 ml |
| Temperature | 37° C. |

When flow rates, temperature, and pH are steady and at targeted values the slider valve on Cell 1 is opened and the rod pushed down to introduce the dosage form into the media in Cell 1. The dosage form swells, and is retained, in the basket. The active ingredient is slowly released into the fluid under conditions that simulate the stomach. After 2 hours the basket, now containing the swollen tablet, is lifted to its raised position and the slider valve is closed. The dosage form holder, including the basket, plunger rod and associated fittings, is removed from the slider valve assembly of Cell 1 and installed onto the slider valve assembly of Cell 2. Once in place, the slider valve of Cell 2 is opened and the rod/basket is pushed down to its lowered position so that the partially swollen tablet is now exposed to the media in Cell 2. Active ingredient is now released from the tablet under conditions that simulate the intestines. It is left in this location until the test is ended.

This example demonstrates that the use of two slider valves combined with the plunger/basket assembly of US20070160497(A1) permits the transfer of non-disintegrating dosage forms from Cell 1 to Cell 2 without stopping the flow of fluids and without requiring the opening of the cells.

Example 3

Non-Disintegrating Dosage Form, Coil Instead of Basket

Example 5 is repeated except that the basket is replaced with a steel wire coil to hold the OxyContin™ tablet. The observations and results are the same as in Example 2 except that the tablet swells within the coil. The swollen tablet is retained by the coil. This example demonstrates that a coil can be used as a tablet holder for testing non-disintegrating tablets.

What is claimed is:

1. A dissolution test cell for use with a continuous flow dissolution test apparatus and method wherein a dosage form is contacted with media and the media is analyzed for concentration of an active substance, said dissolution test cell comprising:
   (A) a vessel having a chamber for holding the media and dosage form therein, at least one inlet and at least one outlet, each of said at least one inlet and at least one outlet being in fluid communication with said chamber for passage of media and dissolved materials;
   (B) a tight-fitting lid attached to said vessel for enclosing said chamber and preventing uncontrolled fluid communication between said chamber and the ambient environment, said lid comprising:
      (1) an opening for passage therethrough of a dosage form into said chamber; and
      (2) a slide valve sealingly affixed to said lid proximate said opening and having:
         (a) a planar member which is moveable between an open position, in which fluids and materials are permitted to pass through said opening and into said chamber, and a closed position, in which fluids and materials are prevented from passing through said opening;
         (b) an actuator in communication with said planar member and being externally accessible for moving said planar member between its open and closed positions during operation of said dissolution test cell;
   (C) a dosage form holder having a compartment and which is removably and sealingly attached to said slide valve assembly,
      wherein, when said planar member of said slide valve assembly is in its open position, the compartment is in fluid communication with said opening and said chamber, whereby a dosage form is permitted to pass from said compartment, through said opening of said lid, and into said chamber; and
   (D) a mixing device for mixing the media, dosage form and dissolved materials in said chamber.

2. The dissolution test cell according to claim 1, wherein said planar member of said slide valve assembly has an opening therethrough which is sized and shaped to align with said opening of said lid when said planar member is in its open position, whereupon said dosage form is permitted to pass through said openings, and a solid portion which sealingly blocks fluid communication with said opening of said lid when said planar member is in its closed position.

3. The dissolution test cell according to claim 1, wherein said slide valve further comprises a threaded annular sleeve aligned with said opening of said lid and said dosage form holder comprises a hollow cap sized and shaped to receive a dosage form thereunder and having an annular threaded interior surface which cooperates with said annular threaded sleeve of said slide valve assembly to removably and sealingly attach said hollow cap to said sliding valve assembly.

4. The dissolution test cell according to claim 1, wherein said slide valve further comprises a threaded annular sleeve aligned with said opening of said lid and said dosage form holder comprises a dosage form holder which comprises:
   (A) a hollow tower portion having an interior cylindrical passage and an internal annular threaded surface which cooperates with the threaded sleeve of the slide valve assembly to removably and sealingly attach said sample holder device to said slide valve assembly;

(B) a plunger disposed in said cylindrical passage of the tower, said plunger being slidable between a raised position and an extended position; and (C) a basket attached to the distal end of the plunger for holding a dosage form;

wherein when the plunger is in its raised position the basket is outside the chamber, and when the plunger is in its extended position the basket is in the chamber and in contact with media therein.

5. A dissolution test apparatus comprising one or more cells in accordance with claim 1.

6. A dissolution test apparatus in which a dosage form is contacted with media and the media is analyzed for concentration of an active substance, said apparatus comprising a first dissolution test cell according to claim 1 and having a first chamber which is connected in series to at least a second dissolution test cell according to claim 1 and having a second chamber, wherein the first dissolution test cell is capable of transferring solid test samples to the second dissolution test cell and the second dissolution test cell is capable of retaining the solid test samples; a first reservoir and at least a second reservoir for continuously supplying one or more media into the first chamber and the second chamber, respectively, the chambers each having a stirrer for mixing the solid test samples and the media together; wherein the second chamber has a filter membrane overlying a base of the second chamber; and a processor for analyzing an effluent from the chambers.

\* \* \* \* \*